US010376459B2

(12) United States Patent
Saquet-Gouville et al.

(10) Patent No.: US 10,376,459 B2
(45) Date of Patent: Aug. 13, 2019

(54) COMBINATION OF ACTIVE AGENTS COMPRISING AT LEAST ONE ESSENTIAL OIL, ONE CYCLODEXTRIN AND ONE LIQUID FATTY SUBSTANCE AND COMPOSITION COMPRISING IT

(71) Applicant: L'OREAL, Paris (FR)

(72) Inventors: Cécile Saquet-Gouville, Vauhallan (FR); Olga Biganska, Bourg la Reine (FR); Catherine Marion, Antony (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/654,691

(22) PCT Filed: Dec. 19, 2013

(86) PCT No.: PCT/IB2013/061146
§ 371 (c)(1),
(2) Date: Jun. 22, 2015

(87) PCT Pub. No.: WO2014/097213
PCT Pub. Date: Jun. 26, 2014

(65) Prior Publication Data
US 2016/0000685 A1 Jan. 7, 2016

Related U.S. Application Data

(60) Provisional application No. 61/751,028, filed on Jan. 10, 2013.

(30) Foreign Application Priority Data

Dec. 21, 2012 (FR) ..................... 12 62707

(51) Int. Cl.
| | | |
|---|---|---|
| *A61K 8/04* | (2006.01) | |
| *A61K 8/73* | (2006.01) | |
| *A61K 8/31* | (2006.01) | |
| *A61K 8/34* | (2006.01) | |
| *A61K 8/37* | (2006.01) | |
| *A61Q 15/00* | (2006.01) | |
| *A61K 8/92* | (2006.01) | |
| *A61Q 13/00* | (2006.01) | |
| *C11B 9/00* | (2006.01) | |
| *A61Q 17/04* | (2006.01) | |
| *A61Q 19/08* | (2006.01) | |

(52) U.S. Cl.
CPC ............. *A61K 8/738* (2013.01); *A61K 8/31* (2013.01); *A61K 8/342* (2013.01); *A61K 8/37* (2013.01); *A61K 8/375* (2013.01); *A61K 8/922* (2013.01); *A61Q 13/00* (2013.01); *A61Q 15/00* (2013.01); *A61Q 17/04* (2013.01); *A61Q 19/08* (2013.01); *C11B 9/00* (2013.01); *A61K 2800/56* (2013.01); *A61K 2800/591* (2013.01); *A61K 2800/805* (2013.01)

(58) Field of Classification Search
CPC .............................. A61K 8/738; A61K 36/53
See application file for complete search history.

(56) References Cited

U.S. PATENT DOCUMENTS

| | | | | |
|---|---|---|---|---|
| 5,605,651 A | * | 2/1997 | Balzer | A61K 8/062 424/401 |
| 6,025,510 A | | 2/2000 | Wimmer et al. | |
| 6,123,932 A | | 9/2000 | Guskey et al. | |
| 6,350,459 B1 | * | 2/2002 | Suzuki | A61K 8/738 424/401 |
| 6,423,329 B1 | | 7/2002 | Sine et al. | |
| 2004/0176265 A1 | * | 9/2004 | Milius | A61K 8/342 510/470 |
| 2005/0266102 A1 | * | 12/2005 | Bahash | A23L 27/00 424/725 |
| 2006/0120967 A1 | * | 6/2006 | Namburi | A61K 9/0043 424/45 |
| 2012/0107252 A1 | | 5/2012 | Laza-Knoerr et al. | |

FOREIGN PATENT DOCUMENTS

| | | | | | |
|---|---|---|---|---|---|
| DE | 19746284 A1 | * | 4/1999 | ............. | A61K 8/738 |
| FR | 2898817 A1 | | 9/2007 | | |
| JP | 63035517 A | * | 2/1988 | | |
| JP | H11-322580 A | | 11/1999 | | |
| KR | 2002-0057448 A | | 7/2002 | | |
| WO | 97/32569 A1 | | 9/1997 | | |
| WO | WO 2004035071 A1 | * | 4/2004 | ........... | A61K 31/724 |
| WO | WO-2011144519 A1 | * | 11/2011 | ............... | A61K 8/31 |

OTHER PUBLICATIONS

Mohacsi-Farkas et al., Proc. Int. Conf. on MAP, Acta Hort. (2003) pp. 199-204.*
Ayala-Zavala et al., J. Incl. Phenom. Macrocycl Chem, 60: 359-368 (2008).*
JPO translation JP, 63-35517, downloaded Aug. 22, 2016 from https://www4.j-platpat.inpit.go.jp.*
Wacker, CAVAMAX Cyclodextrin solutions, (2013) accessed at https://www.wacker.com/cms/media/publications/downloads/6750_EN.pdf, Aug. 22, 2016.*
Berndt et al., EPO machine translation of DE19746284A1, accessed at http://translationportal.epo.org/emtp/translate/?ACTION=description-retrieval&COUNTRY=DE&ENGINE=google&FORMAT=docdb&KIND=A1&LOCALE=en_EP&NUMBER=19746284&OPS=ops.epo.org/3.2&SRCLANG=de&TRGLANG=en accessed Aug. 2017.*

(Continued)

*Primary Examiner* — Susan T Tran
(74) *Attorney, Agent, or Firm* — Joel S. Armstrong

(57) ABSTRACT

The present invention relates to a combination of active agents comprising at least one essential oil, at least one cyclodextrin and at least one liquid fatty substance, the cyclodextrin/essential oil weight ratio ranging from 5 to 12, and to its process of preparation. The present invention also relates to a composition comprising, in a physiologically acceptable medium, such a combination of active agents, and to its process of preparation.

21 Claims, No Drawings

(56) References Cited

OTHER PUBLICATIONS

Apr. 29, 2014 International Search Report issued in International Application No. PCT/IB2013/061146.
Martin Del Valle et al., "Cyclodextrins and their uses: a review," Process Biochemistry, vol. 39, No. 9, May 1, 2014, pp. 1033-1046.
Songkro et al., "Investigation of Inclusion Complexes of Citronella Oil, Citronellal and Citronellol with Beta-Cyclodextrin for Mosquito Repellent," J Incl Phenom Macrocycl Chem, vol. 72, pp. 339-255, 2012.

* cited by examiner

COMBINATION OF ACTIVE AGENTS COMPRISING AT LEAST ONE ESSENTIAL OIL, ONE CYCLODEXTRIN AND ONE LIQUID FATTY SUBSTANCE AND COMPOSITION COMPRISING IT

The invention relates to the field of essential oils.

Essential oils are commonly employed in a great number of fields, such as perfumery, flavours and cosmetics, for their many properties: scenting, antiseptic, soothing, toning, mosquito-repellent or anti-inflammatory.

They are thus frequently employed in compositions intended to prevent and/or treat skin problems, such as juvenile acne or eczema; in caring for the body, for example for soothing pain or simple troublesome conditions due to sunstroke, blisters, cuts or surface wounds; to prevent and/or treat circulatory disorders, such as slight haemorrhages, haemorrhoids or rosacea; and also in caring for the mouth, for the hair, declines in form or in tonicity, and in skin beauty products.

In addition, these essential oils are widely used in perfumery as a result of their high volatility, which makes it possible to obtain a powerful odorous effect even at very low concentrations.

However, with the exception of the cases where essential oils are employed for their scenting properties or to combat insects, their high volatility presents a number of problems.

This is because, as a result of this high volatility, it is necessary to introduce a greater amount of essential oil into the products comprising it, and in particular into cosmetic and/or dermatological compositions. However, the introduction of a greater amount of essential oil results in a stronger odour, which may be felt to be a nuisance by the people who use these compositions.

Thus, it would be desirable to reduce the volatility of essential oils. This would advantageously make it possible, on the one hand, to retain a greater amount of essential oil on its site of application and thus to increase its effectiveness and, on the other hand, to reduce its olfactory impact, indeed even to confer a pleasant odour on the composition comprising them. To reduce the volatility of essential oils would also make it possible to reduce the cost price of the compositions comprising them.

The technical problem at the source of the present invention is to succeed in reducing the volatility of an essential oil, making it possible to obtain a more pleasant attenuated olfactory outcome, while retaining, indeed even improving, the cosmetic qualities of the compositions in which an essential oil is employed.

In addition, in the field of deodorants, a search is always underway for compositions which make it possible to mask, absorb, improve and/or reduce the unpleasant odour resulting from the decomposition of human sweat by bacteria, indeed even to confer a pleasant odour on the body.

Surprisingly, the inventors have demonstrated that the use of a combination of active agents composed of a liquid fatty substance, in particular of a fatty alcohol, of an essential oil and of a cyclodextrin makes it possible to solve these problems.

Thus, the combination of active agents in accordance with the invention advantageously makes it possible to reduce the volatility of an essential oil while reducing its deterioration. Furthermore, the introduction of this combination of active agents into a cosmetic composition improves the cosmetic outcome of the said composition.

The combination of active agents according to the invention is advantageously provided in the form of an oily/thick paste. In addition, a composition comprising such a combination of active agents exhibits a pleasant and ready application and then, once applied, it does not exhibit a rough or squeaky finish.

The composition obtained after introduction of the combination of active agents according to the invention has satisfactory sensory properties in terms of slip on application, of speed of penetration and of skin finish, that is to say that the result obtained is neither tacky nor greasy nor rough. In addition, it has a pleasant odour.

According to a first of its aspects, a subject-matter of the invention is a combination of active agents comprising at least one essential oil, at least one cyclodextrin and at least one liquid fatty substance, characterized in that the cyclodextrin/essential oil weight ratio ranges from 5 to 12.

The present invention also relates to a process for the preparation of a combination of active agents according to the invention, comprising the stages of:
mixing the essential oil with the liquid fatty substance, and
adding the cyclodextrin,
then mixing.

Thus, the present invention also relates to a combination of active agents capable of being obtained according to this process.

Such a process according to the invention does not consist of an encapsulation of the essential oil but of a premix. Thus, without wishing to be committed to a specific theory, the studies of the inventors appear to make it possible to hypothesize that this premix results in the specific properties of the invention which are indicated above.

Within the meaning of the present invention, the term "premix" is understood to mean the mixture of the essential oil with the liquid fatty substance, in the absence of cyclodextrin, obtained on conclusion of the first stage of the process indicated above. This premix is subsequently mixed with the cyclodextrin.

The analysis of the cosmetic products comprising the free essential oil/the essential oil in the premix shows:
a reduction in odour (olfactory evaluation),
a reduction in the volatility of the essential oil (chemical analysis), and
a better stability of the essential oil.

Advantageously, such a process furthermore comprises a final stage of introduction of the combination of active agents thus obtained into the composition in accordance with the invention as defined below.

Such a combination of active agents is advantageously employed in a cosmetic composition.

The cosmetic composition according to the invention exhibits the same advantages as the combination of active agents in accordance with the invention.

Thus, the present invention relates to a cosmetic and/or dermatological composition comprising, in a physiologically acceptable medium, a combination of active agents in accordance with the invention.

In addition, the present invention relates to a process for the preparation of a composition according to the invention comprising the preparation of a combination of active agents according to the following stages:
mixing the essential oil with the liquid fatty substance,
adding the cyclodextrin,
then mixing, and
introducing this combination of active agents into a cosmetic or dermatological composition comprising a physiologically acceptable medium.

Preferably, the optional additional active agents of the cosmetic or dermatological composition are present in the composition before the introduction of the combination of active agents.

The composition according to the invention can advantageously be employed for the purposes of preventing and/or treating elderly skin and/or cutaneous signs of ageing.

Thus, the present invention discloses the use of the composition according to the invention for preventing and/or treating elderly skin and/or cutaneous signs of ageing.

This composition can be used in virtually all cosmetic products: emulsions, gels acting as bases for creams, for milks, for lotions, this being the case whatever their indication: anti-ageing products, products for greasy skin, hygiene products (deodorants) and/or hair products (for combating hair loss or dandruff).

Thus, the examples presented in the present patent application demonstrate that a composition comprising a combination of active agents according to the invention advantageously:

makes possible a reduction in axillary odours, and
makes it possible to render axillary odours more agreeable (olfactory evaluation).

Essential Oils

Essential oils differ from vegetable oils in that they cannot be decomposed by saponification into glycerol and fatty acid soap. Moreover, they are volatile.

According to the definition given in International Standard ISO 9235 and adopted by the Commission of the European Pharmacopoeia, an essential oil is a product, generally of complex composition, obtained from a botanically defined plant starting material, either by steam distillation, or by dry distillation, or by extraction using liquid or gaseous solvents, or via an appropriate mechanical process without heating (cold expression). The essential oil is generally separated from the aqueous phase via a physical process which does not result in any significant change in the composition. These essential oils can also be prepared by synthesis.

The essential oil used according to the invention can be obtained from any plant material resulting from the whole plant or from any part of the said plant, such as, for example, the leaves, stems, flowers, petals, seeds, fruits, buds, roots, branches of plants and/or whole plants.

The essential oil used according to the invention can be prepared according to the abovementioned techniques and will preferably be obtained according to the conventional steam distillation technique.

The essential oil preferably employed in the combinations of active agents of the invention is chosen from geranium essential oil, citronella essential oil, cedar essential oil, sweet orange essential oil, Greek oregano essential oil, lemongrass essential oil, lemon catnip essential oil, rosemary essential oil, winter savory essential oil, thyme essential oil, lemon balm essential oil, lemon essential oil, eucalyptus, in particular radiata or globulus, essential oil, green or red mandarin essential oil, clove essential oil, cinnamon essential oil or their mixtures. Preferably, it is chosen from geranium essential oil, sweet orange essential oil and Greek oregano essential oil.

The combination of active agents according to the invention comprises between 0.00001% and 20% by weight, indeed even between 0.0001% and 10% by weight, of essential oil, with respect to the total weight of the combination.

Geranium Essential Oil

According to a preferred embodiment, the combination of active agents according to the invention comprises geranium essential oil.

The geranium is a herbaceous plant belonging to the family of the Geraniaceae.

Geranium essential oil is mainly available under 2 varieties, namely *Pelargonium roseum asperum* cv. Bourbon and *Pelargonium roseum asperum* cv. North Africa (Egypt).

Their INCI name is identical, namely *Pelargonium graveolens*. Thus, reference is also made to *pelargonium* essential oil. In the present text, the expressions "geranium essential oil" and "*pelargonium* essential oil" are used without distinction in meaning.

Geranium essential oil essentially comprises the combination of 3 monoterpenols, namely citronellol (18% to 32%), geraniol (8% to 20%) and linalol (1.8% to 11%), and of the corresponding terpene esters.

Geranium essential oil is prepared by conventional distillation by steam distillation starting from geranium leaves and stems.

Steam distillation corresponds to the vaporization, in the presence of steam, of a substance which is not very miscible with water. The starting material is brought into contact with water brought to boiling point or with steam in a still. The steam entrains the essential oil vapour, which is condensed in the condenser in order to be recovered as liquid phase in a Florentine flask (or essence jar), where the essential oil is separated from the water by settling. The term "aromatic water" or "hydrolat" or "distilled floral water" is used to describe the aqueous distillate which remains after the steam distillation, once the essential oil has been separated.

Mention may be made, as example of geranium essential oil according to the present invention, of that sold by Elixens under the name *Pelargonium Graveolens* Flower Oil®.

Citronella Essential Oil

According to a preferred embodiment, the combination of active agents according to the invention comprises citronella essential oil.

Citronella is a large grass, originating from India and south-east Asia, which can reach a height of 1.50 meters. It is composed of narrow and lanceolate leaves, the peduncles of which resemble branches. Its fragrance, reminiscent of the odour of lemon, is the source of the name of the plant. This plant of the tropical regions, originating from India and Sri Lanka, also grows in Africa, South America, Central America and Madagascar. Its essential oil is obtained by distillation of the minced leaves, which are harvested several times a year.

This distillation is carried out without addition of water or steam, in a closed chamber designed so that the liquid is recovered in its bottom part.

Mention may be made, as example of citronella essential oil according to the present invention, of that sold by Elixens under the name Cymbopogon Flexuosus Oil®.

Sweet Orange Essential Oil

According to a preferred embodiment, the combination of active agents according to the invention comprises sweet orange essential oil.

The orange is the fruit of the orange tree (*Citrus sinensis*), which belongs to the family of the Rutaceae. Sweet orange essential oil is preferably obtained by expression (pressing and scraping) of orange peel. Sweet orange essential oil has the INCI name: *Citrus Aurantium Dulcis* Peel Oil.

Mention may be made, as sweet orange essential oil, of the product *Citrus Aurantium Dulcis* Peel Oil, sold by Elixens.

This method of production is generally applied only to citrus fruit (*Citrus* spp.) by mechanical processes at ambient temperature. The principle of the method is as follows: the peel is shredded and the contents of the secretory cavities which have been ruptured are recovered by a physical process. The conventional process consists in exerting an abrasive action over the entire surface of the fruit under a stream of water. After removing the solid waste, the essential oil is separated from the aqueous phase by centrifuging. The majority of industrial plants in fact allow the simultaneous or sequential recovery of the fruit juices and of the essential oil.

Greek Oregano Essential Oil

According to a preferred embodiment, the combination of active agents according to the invention comprises Greek oregano essential oil.

Greek oregano (*Origanum heracleoticum* L.) essential oil is extracted from the flowering aerial parts and is predominantly composed of phenols: carvacrol and thymol, and monoterpenes: para-cymene and gamma-terpinene.

This essential oil is recommended in the context of the treatment of dandruff conditions. It is an anti-infective having a very broad spectrum of action: antibacterial, antiviral, antifungal and antiparasitic which is very powerful. It provides a general tonic effect and additionally has immunostimulating properties but also appetite-stimulating and digestive properties.

Mention may be made, as example of Greek oregano essential oil according to the present invention, of that sold by Elixens under the name *Origanum Heracleoticum* Flower Oil®.

Cedar Essential Oil

According to a preferred embodiment, the combination of active agents according to the invention comprises cedar essential oil.

Cedar is a conifer (*Cedrus*) of the family of the Pinaceae. Cedar essential oil is preferably obtained by steam distillation, which method is explained above. Cedar essential oil has the INCI name: *Cedrus* Atlantica Wood Oil.

Mention may be made, as example of cedar essential oil according to the present invention, of that sold by Elixens under the name *Cedrus* Atlantica Wood Oil®.

Lemon Catnip Essential Oil

According to one embodiment of the invention, the combination of active agents according to the invention comprises lemon catnip (*Nepeta cataria* L. *citriodora* Beck.) essential oil. Such an essential oil suitable for the invention can be obtained by extraction by steam distillation starting from the flowering tops. In particular, a lemon catnip essential oil comprises mainly a mixture of monoterpenols, monoterpenals and terpenes.

Rosemary Essential Oil

According to one embodiment of the invention, the combination of active agents in accordance with the invention comprises rosemary essential oil.

A rosemary (*Rosmarinum officinalis* Chemotype Cineole or *Rosmarinum officinalis* 'pyramidalis') essential oil suitable for the invention can be obtained by extraction by steam distillation starting from the leaves.

A rosemary essential oil, the rosemary being of North Africa type, mainly comprises a mixture of terpene oxides, monoterpenones, monoterpenes, monoterpenols, sesquiterpenes and terpene esters and also traces of verbenone, terpinolene, γ-terpinene, linalol and para-cymene.

Winter Savory Essential Oil

According to one embodiment of the invention, the combination of active agents according to the invention comprises winter savory essential oil.

A winter savory (*Satureja montana* L., *Satureja montana* L. ssp *montana*) essential oil suitable for the invention can be obtained by extraction of the plant and flowers by steam distillation. A winter savory essential oil mainly comprises a mixture of phenols, monoterpenes, sesquiterpenes, terpene oxides and monoterpenols.

Thyme Essential Oil

According to one embodiment of the invention, the combination of active agents according to the invention comprises thyme essential oil.

A thyme (*Thymus vulgaris* CT thymol) essential oil suitable for the invention can be obtained by steam distillation of the flowering tops of the plant. In particular, a thymol thyme essential oil mainly comprises phenols (thymol and carvacrol) and alcohols (terpinene and borneol).

Lemon Balm Essential Oil

According to one embodiment of the invention, the combination of active agents according to the invention comprises lemon balm essential oil.

A lemon balm (*Melissa officinalis* L.) essential oil suitable for the invention can be obtained by extraction of the aerial parts by steam distillation. The aerial parts are preferably harvested from June to September. In particular, a lemon balm essential oil mainly comprises a mixture of aldehydes, sesquiterpenes, monoterpenes, terpene esters, alcohols and non-volatile compounds.

Clove Essential Oil

According to one embodiment of the invention, the combination of active agents in accordance with the invention comprises clove essential oil.

A clove (*Eugenia caryophyllus* or *E. aromatica, Syzygium aromaticum*) essential oil suitable for the invention can be obtained by extraction by steam distillation starting from the clove (flower bud). In particular, a clove essential oil mainly comprises a mixture of phenol, sesquiterpenes and esters.

Cinnamon Essential Oil

According to one embodiment of the invention, the combination of active agents in accordance with the invention comprises cinnamon essential oil.

A cinnamon (*Cinnamomum cassia*) essential oil suitable for the invention can be obtained by steam distillation of the bark of the tree. In particular, a cinnamon essential oil mainly comprises an aromatic aldehyde, cinnamaldehyde, and also phenols, such as chavicol and isoeugenol.

Lemon Essential Oil

According to a preferred embodiment, the combination of active agents according to the invention comprises lemon essential oil.

A lemon (*Citrus limonum* L.) essential oil is preferably obtained by expression (pressing and scraping) of lemon peel.

Eucalyptus Essential Oil

According to a preferred embodiment, the combination of active agents according to the invention comprises eucalyptus, preferably radiata or globulus, essential oil.

A eucalyptus (*Eucalyptus radiata* Labill.) essential oil suitable for the invention can be obtained by steam distillation of the leaves of the tree.

Green or Red Mandarin Essential Oil

According to a preferred embodiment, the combination of active agent according to the invention comprises green or red mandarin essential oil.

A green mandarin (Citrus reticulata blanco) essential oil is preferably obtained by expression (pressing and scraping) of mandarin peel.

Cyclodextrin

The combination of active agents according to the invention also comprises at least one cyclodextrin.

The term "cyclodextrin" is understood to mean, within the meaning of the present invention, a cyclodextrin which is not chemically modified.

The cyclodextrins which can be used according to the present patent application are in particular oligosaccharides of formula:

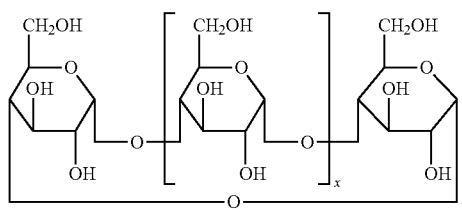

in which x can be a number equal to 4 (which corresponds to α-cyclodextrin), to 5 (β-cyclodextrin) or to 6 (γ-cyclodextrin).

Preferably, the cyclodextrin in accordance with the invention is chosen from β-cyclodextrin and γ-cyclodextrin. Preferably, it is β-cyclodextrin.

Use may in particular be made of a β-cyclodextrin sold by Wacker under the name Cavamax W7 Pharma® and of a γ-cyclodextrin sold by Wacker under the name Cavamax W8®.

The cyclodextrin in accordance with the invention is present in the combination of active agents according to the invention in a content ranging from 30% to 90% by weight, indeed even from 40% to 80% by weight, preferably from 50% to 70% by weight, with respect to the total weight of the combination.

In addition, according to the present invention, the cyclodextrin and the essential oil are present in the combination or the composition according to the invention in a cyclodextrin/essential oil weight ratio of between 5 and 12, preferably of between 8 and 12.

Liquid Fatty Substance

The combination according to the invention also comprises at least one liquid fatty substance.

The term "liquid fatty substance" is understood to mean a compound having a melting point of less than approximately 30-35° C., in contrast to solid fatty substances, such as waxes, which have a melting point of greater than approximately 50° C.

Unless otherwise mentioned, the term "fatty compound", such as, for example, a fatty acid, denotes a compound comprising, in its main chain, at least one saturated or unsaturated hydrocarbon chain, such as alkyl or alkenyl, comprising at least 8 carbon atoms, preferably from 8 to 30 carbon atoms and better still from 10 to 22 carbon atoms.

Preferably, the liquid fatty substances which can be used in the invention are chosen from liquid hydrocarbons, liquid fatty alcohols, liquid fatty esters and silicone oils.

The term "liquid hydrocarbon" is understood to mean a hydrocarbon composed solely of carbon and hydrogen atoms which is liquid at ordinary temperature (25° C.) and at atmospheric pressure (760 mmHg; i.e. $1.013 \times 10^5$ Pa).

More particularly, the liquid hydrocarbons are chosen from:
- linear or branched, optionally cyclic, $C_6$-$C_{16}$ alkanes. Mention may be made, by way of example, of hexane, undecane, dodecane, tridecane or isoparaffins, such as isohexadecane, isododecane and isodecane.
- linear or branched hydrocarbons, of mineral, animal or synthetic origin, having more than 16 carbon atoms, such as liquid paraffins and their derivatives, petrolatum, liquid petrolatum, polydecenes, hydrogenated polyisobutene, such as Parleam®, or squalane.

Squalane is very particularly preferred.

The squalane sold by Croda under the name Pripure 3759® can advantageously be used.

A volatile linear $C_6$-$C_{18}$ alkane or a mixture of such alkanes, such as, for example, a mixture of n-undecane ($C_{11}$) and n-tridecane ($C_{13}$), such as that sold under the reference Cetiol UT by Cognis, can advantageously be used.

The term "liquid fatty alcohol" is understood to mean a non-glycerolated and non-oxyalkylenated fatty alcohol which is liquid at ordinary temperature (25° C.) and at atmospheric pressure (760 mmHg; i.e. $1.013 \times 10^5$ Pa).

Preferably, the liquid fatty alcohols of the invention comprise from 8 to 30 carbon atoms.

The liquid fatty alcohols of the invention can be saturated or unsaturated.

The saturated liquid fatty alcohols are preferably branched. They can optionally comprise, in their structures, at least one aromatic or non-aromatic ring. They are preferably acyclic.

More particularly, the saturated liquid fatty alcohols of the invention are chosen from octyldodecanol, isostearyl alcohol or 2-hexyldecanol.

Octyldodecanol is very particularly preferred.

It can in particular be the octyldodecanol sold by Cognis (BASF) under the name Eutanol G® or that sold by Sasol under the name Isofol 20®.

These unsaturated liquid fatty alcohols exhibit at least, in their structure, at least one double bond or one triple bond. Preferably, the fatty alcohols of the invention have, in their structure, one or more double bonds. When several double bonds are present, there are preferably 2 or 3 of them and they may or may not be conjugated.

These unsaturated fatty alcohols can be linear or branched.

They can optionally comprise, in their structures, at least one aromatic or non-aromatic ring. They are preferably acyclic.

More particularly, the unsaturated liquid fatty alcohols of the invention are chosen from oleyl alcohol, linoleyl alcohol, linolenyl alcohol or undecylenyl alcohol.

Oleyl alcohol is very particularly preferred.

The term "liquid fatty ester" is understood to mean a non-oxyalkylenated ester resulting from a fatty acid and/or a fatty alcohol which is liquid at ordinary temperature (25° C.) and at atmospheric pressure (760 mmHg; i.e. $1.013 \times 10^5$ Pa).

The esters are preferably liquid esters of saturated or unsaturated and linear or branched $C_1$-$C_{26}$ aliphatic mono- or polyacids and of saturated or unsaturated and linear or branched $C_1$-$C_{26}$ aliphatic mono- or polyalcohols, the total number of carbon atoms of the esters being greater than or equal to 10.

Preferably, for the esters of monoalcohols, at least one of the alcohol or of the acid from which the esters of the invention result is branched.

Mention may be made, among the monoesters of monoacids and of monoalcohols, of ethyl palmitate, isopropyl palmitate, alkyl myristates, such as isopropyl myristate or ethyl myristate, isocetyl stearate, 2-ethylhexyl isononanoate, isodecyl neopentanoate or isostearyl neopentanoate.

Use may also be made of esters of $C_4$-$C_{22}$ di- or tricarboxylic acids and of $C_1$-$C_{22}$ alcohols and of esters of mono-, di- or tricarboxylic acids and of di-, tri-, tetra- or pentahydroxy $C_4$-$C_{26}$ non-sugar alcohols.

Mention may in particular be made of: diethyl sebacate; diisopropyl sebacate; di(2-ethylhexyl) sebacate; diisopropyl adipate; di(n-propyl) adipate; dioctyl adipate; di(2-ethylhexyl) adipate; diisostearyl adipate; di(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

The composition can also comprise, as liquid fatty ester, esters and diesters of sugars and of $C_6$-$C_{30}$, preferably $C_{12}$-$C_{22}$, fatty acids. It is recalled that the term "sugar" is understood to mean oxygen-comprising hydrocarbon compounds which have several alcohol functional groups, with or without aldehyde or ketone functional group, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose and lactose, and their derivatives, in particular alkyl derivatives, such as methyl derivatives, for example methylglucose.

The esters of sugars and of fatty acids can be chosen in particular from the group consisting of the esters or mixtures of esters of sugars described above and of saturated or unsaturated and linear or branched $C_6$-$C_{30}$, preferably $C_{12}$-$C_{22}$, fatty acids. If they are unsaturated, these compounds can comprise one to three conjugated or non-conjugated carbon-carbon double bonds.

The esters according to this alternative form can also be chosen from mono-, di-, tri- and tetraesters, polyesters and their mixtures.

These esters can, for example, be oleates, laurates, palmitates, myristates, behenates, cocoates, stearates, linoleates, linolenates, caprates, arachidonates or their mixtures, such as, in particular, mixed oleate/palmitate, oleate/stearate or palmitate/stearate esters.

More particularly, use is made of mono- and diesters and in particular of mono- or di-oleates, -stearates, -behenates, -oleates/palmitates, -linoleates, -linolenates or -oleates/stearates of sucrose, of glucose or of methylglucose.

Mention may be made, by way of example, of the product sold under the name Glucate® DO by Amerchol, which is a methylglucose dioleate.

Finally, use may also be made of the natural or synthetic esters of mono-, di- or triacids with gycerol.

Mention may be made, among these, of vegetable oils.

Mention may be made, as oils of vegetable origin or synthetic triglycerides which can be used in the composition of the invention as liquid fatty esters, for example, of:

triglyceride oils of vegetable or synthetic origin, such as liquid triglycerides of fatty acids comprising from 6 to 30 carbon atoms, such as heptanoic or octanoic acid triglycerides, or alternatively, for example, sunflower oil, maize oil, soybean oil, cucumber oil, grape seed oil, sesame oil, hazelnut oil, apricot oil, macadamia oil, arara oil, castor oil, avocado oil, caprylic/capric acid triglycerides, such as those sold by Stéarinerie Dubois or those sold under the names Miglyol® 810, 812 and 818 by Dynamit Nobel or those sold by Cognis (BASF) under the name Myritol 318®, jojoba oil or shea butter oil.

Preferably, use will be made, as esters according to the invention, of jojoba oil and/or caprylic/capric acid triglycerides. It can also preferably be a sunflower oil, such as, for example, the oil sold under the name Refined Sunflower Oil by Welch, Holme & Clark.

It can in particular be the oil sold by Earth Oil under the name *Simmondsia Chinensis* Oil®.

It can in addition advantageously be the caprylic/capric acid triglycerides sold by Cognis (BASF) under the name Myritol 318®.

The term "liquid silicone" is understood to mean an organopolysiloxane which is liquid at ordinary temperature (25° C.) and at atmospheric pressure (760 mmHg; i.e. $1.013 \times 10^5$ Pa).

Preferably, the silicone is chosen from liquid polydialkylsiloxanes, in particular liquid polydimethylsiloxanes (PDMSs), and liquid polyorganosiloxanes comprising at least one aryl group.

These silicones can also be organomodified. The organomodified silicones which can be used in accordance with the invention are liquid silicones as defined above which comprise, in their structure, one or more organofunctional groups attached via a hydrocarbon group.

Organopolysiloxanes are defined in more detail in the work by Walter Noll, "Chemistry and Technology of Silicones" (1968), Academic Press. They can be volatile or non-volatile, preferably non-volatile.

When they are volatile, the silicones are more particularly chosen from those having a boiling point of between 60° C. and 260° C., and more particularly still from:

(i) cyclic polydialkylsiloxanes comprising from 3 to 7 and preferably from 4 to 5 silicon atoms. They are, for example, octamethylcyclotetrasiloxane, sold in particular under the name Volatile Silicone® 7207 by Union Carbide or Silbione® 70045 V2 by Rhodia, decamethylcyclopentasiloxane, sold under the name Volatile Silicone® 7158 by Union Carbide or Silbione® 70045 V5 by Rhodia, dodecamethylcyclopentasiloxane, sold under the name Silsoft 1217 by Momentive Performance Materials, and their mixtures.

Mention may also be made of cyclocopolymers of the dimethylsiloxane/methylalkylsiloxane type, such as Volatile Silicone® FZ 3109, sold by Union Carbide, of formula:

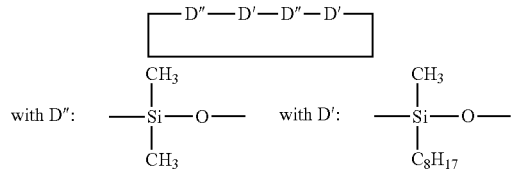

Mention may also be made of mixtures of cyclic polydialkylsiloxanes with organic compounds derived from silicon, such as the mixture of octamethylcyclotetrasiloxane and tetra(trimethylsilyl)pentaerythritol (50/50) and the mixture of octamethylcyclotetrasiloxane and oxy-1,1'-bis(2,2,2', 2',3,3'-hexatrimethylsilyloxy)neopentane;

(ii) volatile linear polydialkylsiloxanes having from 2 to 9 silicon atoms and exhibiting a viscosity of less than or equal to $5 \times 10^{-6}$ m²/s at 25° C. It is, for example, decamethyltetrasiloxane, sold in particular under the name SH 200 by Toray Silicone. Silicones which come within this category are also described in the paper published in Cosmetics and Toiletries, Vol. 91, January 76, pp. 27-32, Todd & Byers, "Volatile Silicone Fluids for Cosmetics". The viscosity of the silicones is measured at 25° C. according to Standard ASTM 445 Appendix C.

Use may also be made of non-volatile polydialkylsiloxanes.

These non-volatile silicones are more particularly chosen from polydialkylsiloxanes, among which mention may be made mainly of polydimethylsiloxanes having trimethylsilyl end groups.

Mention may be made, among these polydialkylsiloxanes, without limitation, of the following commercial products:
the Silbione® oils of the 47 and 70 047 series or the Mirasil® oils sold by Rhodia, such as, for example, the 70 047 V 500 000 oil;
the oils of the Mirasil® series sold by Rhodia;
the oils of the 200 series from Dow Corning, such as DC200, having a viscosity of 60 000 mm²/s;
the Viscasil® oils from General Electric and certain oils of the SF series (SF 96, SF 18) from General Electric.

Mention may also be made of polydimethylsiloxanes having dimethylsilanol end groups known under the name of dimethiconol (CTFA), such as the oils of the 48 series from Rhodia.

The silicones having aryl groups include polydiarylsiloxanes, in particular polydiphenylsiloxanes, and polyalkylarylsiloxanes. Mention may be made, by way of example, of the products sold under the following names:
the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
certain oils of the SF series from General Electric, such as SF 1023, SF 1154, SF 1250 and SF 1265.

The organomodified liquid silicones can in particular have polyethyleneoxy and/or polypropyleneoxy groups. Mention may thus be made of the silicone KF-6017 provided by Shin-Etsu and the oils Silwet® L722 and L77 from Union Carbide.

A liquid fatty substance according to the invention can also be a liquid fatty ether of formula $R_1OR_2$, in which $R_1$ and $R_2$ are linear or branched $C_6$-$C_{18}$, preferably $C_8$-$C_{14}$, alkyl chains. It can preferably be dicaprylyl ether.

The liquid fatty substances in accordance with the invention are preferably chosen from liquid hydrocarbons, liquid fatty alcohols, liquid fatty esters, liquid fatty ethers and silicone oils, and their mixtures.

Thus, the liquid fatty substances in accordance with the invention can preferably be chosen from octyldodecanol, squalane, jojoba vegetable oil, caprylic/capric acid triglycerides, dicaprylyl ether, a mixture of n-undecane ($C_{11}$) and n-tridecane ($C_{13}$), and their mixtures.

Preferably, the liquid fatty substances in accordance with the invention can be chosen from octyldodecanol, squalane, jojoba vegetable oil and caprylic/capric acid triglycerides.

The liquid fatty substance used according to the invention is present in the combination of active agents in a content ranging from 10% to 50% by weight, indeed even from 15% to 40% by weight, preferably from 20% to 30% by weight, with respect to the total weight of the combination of active agents.

Preferably, the content of liquid fatty substance chosen from octyldodecanol, squalane, jojoba vegetable oil, caprylic/capric acid triglycerides and their mixtures in the composition according to the invention is between 0.1% and 5% by weight, with respect to the total weight of the cosmetic composition.

According to a preferred embodiment, the combination of active agents according to the invention comprises, indeed even consists of, an essential oil chosen from geranium essential oil, citronella essential oil, cedar essential oil, sweet orange essential oil, Greek oregano essential oil, lemongrass essential oil, lemon catnip essential oil, rosemary essential oil, winter savory essential oil, thyme essential oil, lemon balm essential oil, lemon essential oil, eucalyptus essential oil, green or red mandarin essential oil, clove essential oil, cinnamon essential oil and their mixtures, cyclodextrin and a liquid fatty substance chosen from octyldodecanol, squalane, jojoba vegetable oil, caprylic/capric acid triglycerides, dicaprylyl ether, a mixture of n-undecane ($C_{11}$) and n-tridecane ($C_{13}$), and their mixtures.

According to an embodiment which is also preferred, the combination of active agents according to the invention comprises, indeed even consists of, an essential oil chosen from geranium essential oil, sweet orange essential oil, lemon essential oil, eucalyptus essential oil, green or red mandarin essential oil, Greek oregano essential oil and their mixtures, β-cyclodextrin and a liquid fatty substance chosen from octyldodecanol, squalane, jojoba vegetable oil, caprylic/capric acid triglycerides, dicaprylyl ether, a mixture of n-undecane ($C_{11}$) and n-tridecane ($C_{13}$), and their mixtures.

Advantageously, the combination of active agents according to the invention comprises a cyclodextrin/essential oil weight ratio approximately equal to 9.

Advantageously, the combination of active agents according to the invention comprises a liquid fatty substance/essential oil weight ratio of between 1 and 10, preferably of between 1 and 5, preferably equal to 3.

Advantageously, the combination of active agents according to the invention comprises a cyclodextrin/liquid fatty substance weight ratio of between 1 and 10, preferably of between 1 and 5, preferably equal to 3.

Composition

According to one aspect of the invention, the combination of active agents in accordance with the invention is advantageously employed in a cosmetic or dermatological composition, in a physiologically acceptable medium. Such a composition is preferably suitable for topical administration.

Such a combination can be introduced into the composition according to the invention, for example into a deodorant product, according to different processes known to a person skilled in the art. Mention may be made, as non-limiting example, of direct introduction into vessel or introduction by suction.

Of course, a person skilled in the art will take care to choose the additional active agents and their amounts so that the advantageous properties of the composition in accordance with the invention are not, or not substantially, detrimentally affected by the envisaged addition.

The cosmetic composition in accordance with the invention advantageously comprises at least one essential oil as defined above in a content of between 0.00001% and 20% by weight, in particular between 0.001% and 10% by weight and preferably between 0.1% and 5% by weight, with respect to the total weight of the composition.

The cosmetic composition in accordance with the invention advantageously comprises at least one cyclodextrin as defined above in a content of between 0.01% and 40% by weight, in particular between 0.1% and 20% by weight and especially between 0.5% and 10% by weight, with respect to the total weight of the composition.

The cosmetic composition in accordance with the invention comprises at least one liquid fatty substance as defined above in a content of between 0.01% and 40% by weight, in particular between 0.1% and 20% by weight and especially between 0.5% and 15% by weight, with respect to the total weight of the composition.

As indicated above, the composition according to the invention is preferably employed topically.

Such compositions can be in the form of a care base for the skin; of a care cream, in particular a day, night or anti-wrinkle cream; of a make-up base; of a deodorant; of a tinted care cream or of a massage oil.

They can in particular be skin care products, such as a protective, treating or care composition for the face, for the hands, for the feet, for the major anatomical folds or for the body (for example, day creams, night cream, make-up-removing cream, anti-sun composition, protective or care body milks, after-sun milks, skin care or scalp care lotion, gel or foam, or artificial tanning composition), an aftershave composition, a deodorant composition or a hair composition.

The composition according to the invention comprises a physiologically or pharmaceutically acceptable medium.

A physiologically acceptable medium is preferably a cosmetically or dermatologically acceptable medium, that is to say a medium which does not have an unpleasant appearance, colour or odour and which is entirely compatible with the administration route under consideration. When the composition is intended to be administered topically, such a medium is regarded as physiologically acceptable when it does not cause any stinging, tautness or redness unacceptable to the user.

The composition according to the invention can be provided in any pharmaceutical dosage form normally used in the cosmetic and dermatological fields.

It can in particular be in the form of an aqueous or aqueous/alcoholic solution which is optionally gelled, of a dispersion of the lotion type, which is optionally a two-phase lotion, of an oil-in-water or water-in-oil or multiple emulsion, of an aqueous gel, of a dispersion of oils in an aqueous phase, preferably using spherules, it being possible for these spherules to be polymer particles or preferably lipid vesicles of ionic and/or non-ionic type, or alternatively in the form of a powder, of a serum, of an oil, of a paste or of a soft stick. It can have a solid, pasty or more or less fluid liquid consistency.

A composition of the invention is preferentially in the form of an aqueous solution.

Thus, the composition can comprise all the constituents usually employed in the envisaged application and the envisaged type of administration.

Mention may in particular be made of water, solvents, oils of mineral, animal and/or vegetable origin, in particular as described in detail above, waxes, in particular as described below, pigments, fillers, surfactants, gelling agents, preservatives and their mixtures, especially water.

Thus, the composition according to the invention can advantageously comprise from 5% to 98% by weight of water, preferably from 50% to 90% by weight of water and preferably from 70% to 90% by weight of water, with respect to the total weight of the composition.

The composition according to the invention can furthermore comprise additional compounds.

Of course, a person skilled in the art will take care to choose this or these optional additional compound(s) and/or their amounts so that the advantageous properties of the composition according to the invention are not, or not substantially, detrimentally affected by the envisaged addition and so that the properties of the compositions resulting therefrom are compatible with the administration route favoured.

The composition according to the invention can additionally comprise waxes.

Mention may be made, as waxes which can be used according to the invention, of waxes of animal origin, such as beeswax, spermaceti, lanolin wax and lanolin derivatives, vegetable waxes, such as carnauba wax, candelilla wax, ouricury wax, Japan wax, cocoa butter, cork fibre wax or sugarcane wax, mineral waxes, for example paraffin wax, petrolatum wax, lignite wax or microcrystalline waxes or ozokerites, or synthetic waxes, including polyethylene wax, polytetrafluoroethylene wax and the waxes obtained by the Fischer-Tropsch synthesis or alternatively silicone waxes, hydrogenated oils which are solid at 25° C., such as hydrogenated castor oil, hydrogenated jojoba oil, hydrogenated palm oil, hydrogenated tallow or hydrogenated coconut oil, and fatty esters which are solid at 25° C., such as the $C_{20}$-$C_{40}$ alkyl stearate sold under the trade name Kester Wax K82H by Koster Keunen.

The compositions according to the invention can comprise a volatile oil other than a liquid fatty substance as defined above.

The term "volatile oil" is understood to mean, within the meaning of the invention, an oil which is capable of evaporating on contact with keratinous substances in less than one hour, at ambient temperature and atmospheric pressure. The volatile organic solvent(s) and the volatile oils of the invention are volatile organic solvents and volatile cosmetic oils which are liquid at ambient temperature and which have a non-zero vapour pressure at ambient temperature and atmospheric pressure ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

Mention may be made, as volatile oils, inter alia, of linear or cyclic silicones including from 2 to 6 silicon atoms, such as cyclohexasiloxane, dodecamethylpentasiloxane, decamethyltetrasiloxane, butyltrisiloxane and ethyltrisiloxane. Use may also be made of branched hydrocarbons, such as, for example, isododecane, and also volatile perfluoroalkanes, such as dodecafluoropentane and tetradecafluorohexane, sold under the names PF 5050® and PF 5060® by 3M, and perfluoromorpholine derivatives, such as 4-(trifluoromethyl) perfluoromorpholine, sold under the name PF 5052® by 3M.

The amount of oily phase present in the compositions according to the invention can range, for example, from 0.01% to 99% by weight and preferably from 0.1% to 30% by weight, with respect to the total weight of the composition.

Of course, within the meaning of the present invention, the amount of oily phase presented above comprises the amount of essential oil and also the liquid fatty substance according to the invention.

According to a specific embodiment, the composition according to the invention can furthermore comprise at least one additional active agent chosen from surfactants, moisturizing agents, anti-wrinkle or anti-ageing agents, UV screening agents, desquamating agents, antioxidants, agents which stimulate the synthesis of dermal and/or epidermal macromolecules, dermo-decontracting agents, depigmenting agents, deodorant agents, fragrances and their mixtures.

These additional active agents can be present in the composition according to the invention in a content ranging from 0.001% to 30% by weight, preferably from 0.01% to 20% by weight and more preferably from 0.1% to 15% by weight, with respect to the total weight of the composition comprising them.

Anti-wrinkle or Anti-ageing Agents

Mention may more particularly be made, by way of representation of anti-wrinkle agents or anti-ageing agents which can be used in the present invention, of adenosine; retinol and its derivatives; ascorbic acid and its derivatives, such as magnesium ascorbyl phosphate and ascorbyl glucoside; tocopherol and its derivatives, such as tocopheryl acetate; nicotinic acid and its precursors, such as nicotinamide; ubiquinone; glutathione and its precursors, such as L-2-oxothiazolidine-4-carboxylic acid; C-glycoside compounds and their derivatives, such as described in particular below; plant extracts and in particular rock samphire and olive leaf extracts, and also plant proteins and their hydrolysates, such as rice or soy protein hydrolysates; or also *Vigna aconitifolia* seed extracts, such as those sold by Cognis under the Vitoptine LS9529 and Vit-A-Like LS9737 references; algal extracts and in particular Laminaria extracts; bacterial extracts; sapogenins, such as diosgenin, and the Dioscoreae extracts, in particular wild yam extracts, comprising the latter; α-hydroxy acids; β-hydroxy acids, such as salicylic acid and 5-(n-octanoyl)salicylic acid; oligopeptides and pseudodipeptides and their acylated derivatives, in particular (2-{acetyl[3-(trifluoromethyl)phenyl]amino}-3-methylbutyrylamino)acetic acid and the lipopeptides sold by Sederma under the trade names Matrixyl 500 and Matrixyl 3000; lycopene; manganese and magnesium salts, in particular the gluconates; and their mixtures.

Humectants or Moisturizing Agents

Mention may in particular be made, as humectants or moisturizing agents, of glycerol, an Aloe Vera extract, urea and its derivatives, in particular Hydrovance®, sold by National Starch, monosaccharides, such as mannose, hyaluronic acid, AHAs, BHAs, acrylic acid homopolymers, such as Lipidure-HM® from NOF Corporation, β-glucan and in particular sodium carboxymethyl β-glucan from Mibelle-AG-Biochemistry; a polyoxybutylene/polyoxyethylene/polyoxypropylene glycerol, such as Wilbride S-753L® from NOF Corporation, a musk rose oil sold by Nestlé; collagen and chondroitin sulfate spheres of marine origin (Atelocollagen), sold by Engelhard Lyon under the name Sphères de Comblement Marines [Marine Filling Spheres]; hyaluronic acid spheres, such as those sold by Engelhard Lyon.

UV Screening Agents

Mention may be made, as non-limiting illustrations of UV screening agents, of anthranilates, in particular menthyl anthranilate; benzophenones, in particular benzophenone-1, benzophenone-3, benzophenone-5, benzophenone-6, benzophenone-8, benzophenone-9, benzophenone-12 and preferably benzophenone-2 (oxybenzone) or benzophenone-4 (Uvinul MS40® available from BASF); benzylidene camphors, in particular 3-benzylidene camphor, benzylidene camphor sulfonic acid, camphor benzalkonium methosulfate, polyacrylamidomethyl benzylidene camphor, terephthalylidene dicamphor sulfonic acid and preferably 4-methylbenzylidene camphor (Eusolex 6300®, available from Merck); benzimidazoles, in particular benzimidazilate (Neo Heliopan AP®, available from Haarmann and Reimer) or phenylbenzimidazole sulfonic acid (Eusolex 232®, available from Merck); benzotriazoles, in particular drometrizole trisiloxane or methylene bis-benzotriazolyl tetramethylbutylphenol (Tinosorb M®, available from Ciba); cinnamates, in particular cinoxate, DEA methoxycinnamate, diisopropyl methyl cinnamate, glyceryl ethylhexanoate dimethoxycinnamate, isopropyl methoxycinnamate, isoamyl cinnamate and preferably etocrylene (Uvinul N35®, available from BASF), octyl methoxycinnamate (Parsol MCX®, available from Hoffman LaRoche) or octocrylene (Uvinul 539®, available from BASF); dibenzoylmethanes, in particular butyl methoxydibenzoylmethane (Parsol 1789®); imidazolines, in particular ethylhexyl dimethoxybenzylidene dioxoimidazoline; PABAs, in particular ethyl dihydroxypropyl PABA, ethylhexyl dimethyl PABA, glyceryl PABA, PABA, PEG-25 PABA and preferably diethylhexyl butamido triazone (Uvasorb HEB®, available from 3V Sigma), ethylhexyl triazone (Uvinul T150®, available from BASF) or ethyl PABA (benzocaine); Mexoryl®; salicylates, in particular dipropylene glycol salicylate, ethylhexyl salicylate, homosalate or TEA salicylate; triazines, in particular anisotriazine (Tinosorb S®, available from Ciba); drometrizole trisiloxane; zinc oxide, titanium dioxide, and coated or uncoated zinc, iron, zirconium or cerium oxide.

Desquamating Agents

Mention will be made, as desquamating agents, of β-hydroxy acids, in particular salicylic acid and its derivatives, other than 5-(n-octanoyl)salicylic acid; urea; glycolic acid, citric acid, lactic acid, tartaric acid, malic acid or mandelic acid; 4-(2-hydroxyethyl)piperazine-1-propanesulfonic acid (HEPES); *Saphora japonica* extract; honey; N-acetylglucosamine; sodium methylglycine diacetate, α-hydroxy acids (AHAs), β-hydroxy acids (BHAs), and their mixtures.

Antioxidants

Mention may more particularly be made, as antioxidants, of tocopherol and its esters, in particular tocopheryl acetate; EDTA; ascorbic acid and its derivatives, in particular magnesium ascorbyl phosphate and ascorbyl glucoside; chelating agents, such as BHT, BHA or N,N'-bis(3,4,5-trimethoxybenzyl)ethylenediamine and its salts, and their mixtures.

Dermo-decontracting or Dermo-relaxing Agents

Mention may very particularly be made, as dermo-decontracting or dermo-relaxing agents, of manganese gluconate, wild yam, rock samphire, glycine and alverine.

Active Agents Which Stimulate the Synthesis of Dermal and/or Epidermal Macromolecules and/or Which Prevent Their Decomposition Mention may be made, as active agents which stimulate the synthesis of dermal and/or epidermal macromolecules and/or which prevent their decomposition, of: peptides extracted from plants, such as the soybean hydrolysate sold by BASF Beauty Care Solutions under the trade name Phytokine®, the malt extract as sold under the name Collalift® by BASF BCS; rice peptides, such as Nutripeptide® from Silab, or alternatively a rice peptide extract, such as Colhibin® from Pentapharm DSM, methylsilanol mannuronate, such as Algisium C®, sold by Exsymol; a *Vaccinium myrfillus* extract, such as those described in Application FR-A-2 814 950; the lupin extract sold by Silab under the trade name Structurine®, and their mixtures, verbena hydrolat.

Depigmenting Agents

Mention may be made, as depigmenting agents, of ceramides, vitamin C and its derivatives and in particular vitamin CG, CP and 3-O-ethyl-vitamin C, α- and β-arbutin, ferulic acid, kojic acid, resorcinol and its derivatives, calcium D-pantetheine sulfonate, lipoic acid, ellagic acid, vitamin B3, phenylethyl resorcinol, such as Symwhite 377® from Symrise, a kiwi fruit (*Actinidia chinensis*) juice sold by Gattefosse, a *Paeonia suffruticosa* root extract, such as that sold by Ichimaru Pharcos under the name Botanpi Liquid B®, a brown sugar (*Saccharum officinarum*) extract, such as the molasses extract sold by Taiyo Kagaku under the name Molasses Liquid, or a mixture of undecylenic acid and undecylenoyl phenylalanine, such as Sepiwhite MSH® from Seppic.

Deodorant Agents

A deodorant agent according to the invention is different from an essential oil, from a cyclodextrin, from a liquid fatty substance or from a mixture of at least 2 of these compounds as described above.

Mention may be made, as deodorant agents in accordance with the invention, of bacteriostatic agents or bactericidal agents which act on the microorganisms of axillary odours, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol).

Deodorant agents in accordance with the invention can also be chosen from quaternary ammonium salts, such as cetyltrimethylammonium salts, cetylpyridinium salts, DPTA (1,3-diaminopropanetetraacetic acid), 1,2-decanediol (Symclariol from Symrise), glycerol derivatives, such as, for example, caprylic/capric glycerides (Capmul MCM from Abitec), glyceryl caprylate or caprate (Dermosoft GMCY and Dermosoft GMC, respectively from Straetmans) or polyglyceryl-2 caprate (Dermosoft DGMC from Straetmans), biguanide derivatives, such as polyhexamethylene biguanide salts, chlorhexidine and its salts, and 4-phenyl-4,4-dimethyl-2-butanol (Symdeo MPP from Symrise).

Mention may also be made, as deodorant agents, of zinc salts, such as zinc salicylate, zinc gluconate, zinc pidolate, zinc sulfate, zinc chloride, zinc lactate or zinc phenolsulfonate, or salicylic acid and its derivatives, such as 5-(n-octanoyl)salicylic acid.

In addition, deodorant agents according to the invention can be chosen from odour absorbers, such as zinc ricinoleate, sodium bicarbonate, metallic or non-metallic zeolites, cyclodextrins and alum.

They can also be a chelating agent, such as Dissolvine GL-47-S from Akzo Nobel, EDTA or DPTA.

They can also be polyols, such as glycerol or 1,3-propanediol (Zemea Propanediol, sold by Dupont Tate and Lyle Bio Products), or an enzyme inhibitor, such as triethyl citrate.

In the event of incompatibility or in order to stabilize them, some of the abovementioned agents can be incorporated into spherules, in particular ionic or non-ionic vesicles, and/or particles (capsules and/or spheres).

Of course, the deodorant agents which may be present in a composition in accordance with the invention must not detrimentally affect the advantageous properties of the composition which are indicated above.

The composition according to the invention can advantageously be provided in the form of an emulsion, obtained in particular by dispersion of an aqueous phase in a fatty phase (W/O) or of a fatty phase in an aqueous phase (O/W), of liquid or semi-liquid consistency of the milk type, or of soft, semi-solid or solid consistency of the cream or gel type or in the form of a stick, or alternatively of a multiple emulsion (W/O/W or O/W/O). These compositions are prepared according to the usual methods.

A composition of this type can have the form of a care or make-up product for the face and/or body and can be packaged, for example, in the form of a cream in a jar or of a fluid in a tube or in a pump-action spray.

The emulsions according to the invention can comprise at least one emulsifier chosen from amphoteric, anionic, cationic or non-ionic emulsifiers, used alone or as a mixture.

Advantageously, the emulsifiers are appropriately chosen according to the emulsion to be obtained (W/O or O/W). The emulsifiers are generally present in the composition in a proportion which can range from 0.3% to 30% by weight and preferably from 0.5% to 10% by weight, with respect to the total weight of the composition.

Mention may be made, for the O/W emulsions, for example, as emulsifiers, of non-ionic surfactants and in particular esters of polyols and of fatty acid having a saturated or unsaturated chain comprising, for example, from 8 to 24 carbon atoms and better still from 12 to 22 carbon atoms, and their oxyalkylenated derivatives, that is to say derivatives comprising oxyethylene and/or oxypropylene units, such as glyceryl esters of $C_8$-$C_{24}$ fatty acid, and their oxyalkylenated derivatives; polyethylene glycol esters of $C_8$-$C_{24}$ fatty acid, and their oxyalkylenated derivatives; sorbitol esters of $C_8$-$C_{24}$ fatty acid, and their oxyalkylenated derivatives; sugar (sucrose, glucose, alkylglucose) esters of $C_8$-$C_{24}$ fatty acid, and their oxyalkylenated derivatives; fatty alcohol ethers; sugar ethers of $C_8$-$C_{24}$ fatty alcohols; and their mixtures.

The composition according to the invention can additionally comprise at least one silicone elastomer, such as the products sold under the KSG names by Shin-Etsu, under the Trefil, BY29 or EPSX names by Dow Corning or under the Gransil names by Grant Industries.

The composition according to the invention can additionally comprise at least one colourant chosen, for example, from pigments, pearlescent agents, dyes, effect materials and their mixtures.

The composition according to the invention can additionally comprise at least one filler. These fillers can be inorganic or organic and of any shape, platelet, spherical or oblong, irrespective of the crystallographic form (for example sheet, cubic, hexagonal, orthorhombic or amorphous).

Mention may be made of silica, talc, mica, kaolin, lauroyl lysine, starch, boron nitride, PTFE powders, PMMA powders, methylsilsesquioxane resin powders (such as Tospearl 145A from GE Silicone), hollow silicone resin hemispherical particles (such as NLK 500, NLK 506 and NLK 510 from Takemoto Oil and Fat), barium sulfate, precipitated calcium carbonate, magnesium carbonate, basic magnesium carbonate, hydroxyapatite, glass or ceramic microcapsules, or metal soaps derived from organic carboxylic acids having from 8 to 22 carbon atoms and preferably from 12 to 18 carbon atoms, for example zinc stearate, magnesium stearate, lithium stearate, zinc laurate or magnesium myristate.

The composition according to the invention can additionally comprise various adjuvants commonly used in the cosmetics field, such as sequestering agents, fragrances, and thickening and gelling agents.

Of course, a person skilled in the art will take care to choose this or these optional adjuvant(s) and/or their amounts so that the advantageous properties of the composition are not, or not substantially, detrimentally affected by the envisaged addition and so that they are also compatible with the administration route under consideration.

The composition according to the invention can be manufactured by any known process generally used in the cosmetics or dermatology fields.

Throughout the description, including the claims, the expression "comprising a" should be understood as being synonymous with "comprising at least one", unless otherwise specified.

The expressions "between . . . and . . . " and "ranging from . . . to . . . " should be understood as meaning limits included, unless otherwise specified.

The examples which follow are presented by way of illustration and without implied limitation of the invention. The percentages are expressed by weight of starting materials. The compounds are, as the case may be, mentioned as chemical names or as CTFA (International Cosmetic Ingredient Dictionary and Handbook) names.

EXAMPLES

Example 1

Process for Producing a Combination of Active Agents According to the Invention 7 g of geranium essential oil (HE Geranium Egypte Bio, Elixens) are mixed with 20 g of octyldodecanol (Eutanol G, Cognis (BASF)). This premix is poured directly onto 73 g of β-cyclodextrin (Cavamax W7 Pharma, Wacker).

Slow homogenization is carried out in order to intimately mix all the ingredients.

The combination of active agents thus obtained can subsequently be introduced at the end of manufacture into any cosmetic composition, at an ambient temperature.

Example 2

Comparative Tests on the Olfactory and Cosmetic Outcomes

Composition 3 comprises a combination of active agents according to the invention prepared, *mutatis mutandis*, according to the protocol of Example 1.

| Compounds | Comparative Composition 1 (% by weight, with respect to the total weight of the composition) | Comparative Composition 2 (% by weight, with respect to the total weight of the composition) | Composition 3 In accordance with the invention (% by weight, with respect to the total weight of the composition) |
|---|---|---|---|
| Phenoxyethanol (and) methylparaben (and) ethylparaben (and) propylparaben (and) isobutylparaben (and) butylparaben Phenonip, Clariant | 0.5 | 0.5 | 0.5 |
| Octyldodecanol Eutanol G, Cognis (BASF) | — | — | 1.8 |
| *Geranium* essential oil HE *Geranium* Egypte Bio, Elixens | 0.6 | 0.6 | 0.6 |
| Xanthan gum Keltrol CG-T, CP Kelco | 1 | 1 | 1 |
| Cyclodextrin Cavamax W7 Pharma, Wacker | — | 5.4 | 5.4 |
| Polysorbate 20 Tween 20-LQ-(WL), Croda | 1 | 1 | 1 |
| Water | 96.9 | 91.5 | 89.7 |
| Olfactory outcome | Intensity+++ | Unpleasant odour | Intensity+; More pleasant, more floral, rounder odour |

The olfactory and cosmetic outcomes of the 3 cosmetic compositions indicated above were compared.

Comparative composition 1, comprising geranium essential oil, in the absence of cyclodextrin, or of one of its derivatives, and of a liquid fatty substance, is the reference composition with which the outcomes of the 2 other compositions will be compared.

As indicated above in the present patent application, comparative composition 2, which comprises geranium essential oil and cyclodextrin but no liquid fatty substance according to the invention, makes it possible to significantly reduce the olfactory outcome in comparison with that of comparative composition 1; however, comparative composition 2 exhibits an unpleasant odour.

This decrease in the volatility of the geranium essential oil is, however, accompanied by a strong deterioration in the cosmetic outcome of comparative composition 2, in comparison with that of composition 1.

Composition 3 in accordance with the invention consequently comprises geranium essential oil, cyclodextrin and octyldodecanol.

In addition to a significant reduction in the olfactory outcome of composition 3 in comparison with that of comparative composition 1, the cosmetic outcome of this composition is also better than that of comparative composition 2, which does not comprise octyldodecanol. Composition 3 in accordance with the invention also exhibits a more pleasant odour than compositions 1 and 2.

Furthermore, composition 3 in accordance with the invention exhibits satisfactory cosmetic properties in terms of slip on application, of speed of penetration and of skin finish, that is to say that the result obtained is neither tacky nor greasy nor rough.

Example 3a

Tests on the Olfactory and Cosmetic Outcomes of Compositions in Accordance with the Invention Compositions 4 and 5 comprise a combination of active agents according to the invention prepared, *mutatis mutandis,* according to the protocol of Example 1.

| Compounds | Composition 4 in accordance with the invention (% by weight, with respect to the total weight of the composition) | Composition 5 in accordance with the invention (% by weight, with respect to the total weight of the composition) |
|---|---|---|
| Phenoxyethanol (and) methylparaben (and) ethylparaben (and) propylparaben (and) isobutylparaben (and) butylparaben Phenonip, Clariant | 0.5 | 0.5 |
| Octyldodecanol Eutanol G, Cognis (BASF) | 1.8 | — |
| Squalane Pripure 3759, Croda | — | 1.8 |
| *Geranium* essential oil HE *Geranium* Egypte Bio, Elixens | 0.6 | 0.6 |
| Xanthan gum Keltrol CG-T, CP Kelco | 1 | 1 |
| Cyclodextrin Cavamax W7 Pharma, Wacker | 5.4 | 5.4 |
| Polysorbate 20 Tween 20-LQ-(WL), Croda | 1 | 1 |
| Water | 89.7 | 89.7 |

These two compositions in accordance with the invention exhibit satisfactory cosmetic properties in terms of slip on application, of speed of penetration and of skin finish, that is to say that the result obtained is neither tacky nor greasy nor rough.

In addition, they have a pleasant odour.

Example 3b

Tests on the Olfactory and Cosmetic Outcomes of Compositions in Accordance with the Invention Compositions 6 and 7 comprise a combination of active agents according to the invention prepared, *mutatis mutandis,* according to the protocol of Example 1.

| Compounds | Composition 6 in accordance with the invention (% by weight, with respect to the total weight of the composition) | Composition 7 in accordance with the invention (% by weight, with respect to the total weight of the composition) |
|---|---|---|
| Phenoxyethanol (and) methylparaben (and) ethylparaben (and) propylparaben (and) isobutylparaben (and) butylparaben Phenonip, Clariant | 0.5 | 0.5 |
| Jojoba vegetable oil *Simmondsia Chinensis* Oil Earth Oil | 1.8 | — |
| Squalane Pripure 3759, Croda | — | 1.8 |
| Sweet orange essential oil *Citrus Aurantium Dulcis* Peel Oil Elixens | 0.6 | 0.6 |
| Xanthan gum Keltrol CG-T, CP Kelco | 1 | 1 |
| Cyclodextrin Cavamax W7 Pharma, Wacker | 5.4 | 5.4 |
| Polysorbate 20 Tween 20-LQ-(WL), Croda | 1 | 1 |
| Water | 89.7 | 89.7 |

These two compositions in accordance with the invention exhibit satisfactory cosmetic properties in terms of slip on application, of speed of penetration and of skin finish, that is to say that the result obtained is neither tacky nor greasy nor rough.

In addition, they have a pleasant odour.

Example 3c

Tests on the Olfactory and Cosmetic Outcomes of Compositions in Accordance with the Invention Compositions 8 to 11 comprise a combination of active agents according to the invention prepared, *mutatis mutandis,* according to the protocol of Example 1.

| Compounds | Composition 8 in accordance with the invention (% by weight, with respect to the total weight of the composition) | Composition 9 in accordance with the invention (% by weight, with respect to the total weight of the composition) | Composition 10 in accordance with the invention (% by weight, with respect to the total weight of the composition) | Composition 11 in accordance with the invention (% by weight, with respect to the total weight of the composition) |
|---|---|---|---|---|
| Phenoxyethanol (and) methylparaben | 0.5 | 0.5 | 0.5 | 0.5 |

| Compounds | Composition 8 in accordance with the invention (% by weight, with respect to the total weight of the composition) | Composition 9 in accordance with the invention (% by weight, with respect to the total weight of the composition) | Composition 10 in accordance with the invention (% by weight, with respect to the total weight of the composition) | Composition 11 in accordance with the invention (% by weight, with respect to the total weight of the composition) |
|---|---|---|---|---|
| (and) ethylparaben (and) propylparaben (and) isobutylparaben (and) butylparaben Phenonip, Clariant | | | | |
| Jojoba vegetable oil *Simmondsia Chinensis* Oil Earth Oil | 1.8 | — | — | — |
| Octyldodecanol Eutanol G, Cognis (BASF) | — | 1.8 | — | — |
| Caprylic/capric acid triglycerides Myritol 318 Cognis (BASF) | — | — | 1.8 | — |
| Squalane Pripure 3759, Croda | — | — | — | 1.8 |
| Greek oregano essential oil *Origanum Heracleoticum* Flower Oil Elixens | 0.6 | 0.6 | 0.6 | 0.6 |
| Xanthan gum Keltrol CG-T, CP Kelco | 1 | 1 | 1 | 1 |
| Cyclodextrin Cavamax W7 Pharma, Wacker | 5.4 | 5.4 | 5.4 | 5.4 |
| Polysorbate 20 Tween 20-LQ-(WL), Croda | 1 | 1 | 1 | 1 |
| Water | 89.7 | 89.7 | 89.7 | 89.7 |

These four compositions in accordance with the invention exhibit satisfactory cosmetic properties in terms of slip on application, of speed of penetration and of skin finish, that is to say that the result obtained is neither tacky nor greasy nor rough.

In addition, they have a pleasant odour.

Example 3d

Tests on the Olfactory and Cosmetic Outcomes of Compositions in Accordance with the Invention Compositions 12 and 13 comprise a combination of active agents according to the invention prepared, *mutatis mutandis*, according to the protocol of Example 1.

| Compounds | Composition 12 in accordance with the invention (% by weight, with respect to the total weight of the composition) | Composition 13 in accordance with the invention (% by weight, with respect to the total weight of the composition) |
|---|---|---|
| Octyldodecanol Isofol 20, Sasol | 0.3 | 3 |
| Sunflower seed oil Refined Sunflower Oil, Welch Holme & Clark | 2 | 2 |
| Petrolatum White Fonoline Sonneborn | 2 | 2 |
| Cera alba White Beeswax SP453P Strahl & Pitsch | 1 | 1 |
| Shea butter Lipex 102 AarhusKarlshamn | 3 | 3 |
| Cetyl alcohol Lanette 16 Cognis (BASF) | 0.5 | 0.5 |
| Myristyl myristate Tegosoft MM Evonik Goldschmidt | 2 | 2 |
| Stearyl alcohol Lanette 18 Cognis (BASF) | 0.5 | 0.5 |
| *Geranium* essential oil *Pelargonium graveolens* flower oil HE *Geranium* Egypte Bio Elixens | 0.1 | 1 |
| Acrylamide/sodium acryloyl-dimethyl taurate copolymer (and) isohexadecane (and) polysorbate 80 Simulgel 600 Seppic | 0.4 | 0.4 |

-continued

| Compounds | Composition 12 in accordance with the invention (% by weight, with respect to the total weight of the composition) | Composition 13 in accordance with the invention (% by weight, with respect to the total weight of the composition) |
|---|---|---|
| Cyclodextrin Cavamax W7 Pharma Wacker | 0.9 | 9 |
| Dimethicone Belsil DM 10 Wacker | 10 | 10 |
| Glycerol Glycerine 4833 Oleon | 10 | 10 |
| Propylene glycol Propylene glycol USP/EP Dow Chemical | 4 | 4 |
| Stearic acid and palmitic acid Palmera B1802CG KLK OLEO | 3 | 3 |
| Glyceryl stearate (and) PEG-100 stearate Simulsol 165 Seppic | 2 | 2 |
| Preservatives, pH agents, fragrance | q.s. | q.s. |
| Water | q.s. 100 | q.s. 100 |

These two compositions in accordance with the invention exhibit satisfactory cosmetic properties in terms of slip on application, of speed of penetration and of skin finish, that is to say that the result obtained is neither tacky nor greasy nor rough.

In addition, they have a pleasant odour.

Example 4

Test on the Axillary Olfactory Outcome of a Composition in Accordance with the Invention The present randomized test is carried out on 20 individuals aged from 18 to 65 years. These people have:
moderately strong axillary odours, i.e. having an intensity greater than or equal to 58 on a scale from 1 (imperceptible) to 9 (extremely strong);
a difference in intensity between the 2 armpits of less than or equal to 1;
and having used a standardized shower gel during the 7 days preceding the test, without application of any other product (cleanser, deodorant, antiperspirant or any other scented product).

After wiping the treated armpit, the test compositions described below were applied thereto in a proportion of 0.4 g+/−0.5 g.

The odour is subsequently evaluated olfactorily by several people, at different times, in order to evaluate:
(i) the intensity of the axillary odour (on a scale ranging from 1=none to 9=extremely strong); and
(ii) the hedonic value of the axillary odour (on a scale ranging from 1=extremely unpleasant to 9=extremely pleasant). The grades obtained are used in order to obtain a mean.

The values shown in the Table below for the intensity and the hedonic value correspond to a percentage difference between the mean of the grades obtained before application of the test composition and the mean obtained after application at the given times.

These evaluations took place 8 h, 24 h and 48 h after application of one of the compositions described below.

Thus, a negative percentage for the intensity indicates a decrease in the intensity of the odour at the treated armpit, in comparison with before the application of the composition. A negative percentage for the hedonic value indicates an odour which has become less pleasant at the treated armpit after application of the composition.

Conversely, a positive percentage for the intensity indicates an increase in the intensity of the odour at the treated armpit, in comparison with before the application of the composition. A positive percentage for the hedonic value indicates an odour which has become more pleasant at the treated armpit after application of the composition.

The test compositions comprise the following mixture of essential oils:

| Mixture of essential oils | % by weight, with respect to the total weight of the mixture |
|---|---|
| Organic lemon peel essential oil (*Citrus medica limonum* peel oil) Lemon Zest Oil Organic - Elixens | 7.14 |
| Organic *eucalyptus radiata* essential oil (*Eucalyptus radiata* oil) | 27.62 |
| Organic clove essential oil (*Eugenia caryophyllus* flower oil) | 2.04 |
| Organic lemongrass essential oil (*Cymbopogon flexuosus* oil) | 10.2 |
| Organic green mandarin essential oil (*Citrus nobilis* peel oil) Green mandarin oil Organic - Elixens | 13.26 |
| Organic rosemary cineole essential oil (*Rosmarinus officinalis* leaf oil) | 10.2 |
| Organic winter savory essential oil (*Satureja montana* oil) | 2.04 |
| Organic thyme chemotype thymol essential oil (*Thymus vulgaris* oil) | 27.5 |

The compositions employed and the results obtained are as follows:

| | Composition 14 not in accordance with the invention | | Composition 15 in accordance with the invention | |
|---|---|---|---|---|
| Type | O/W emulsion | | O/W emulsion | |
| Composition (% by weight, with respect to the total weight of the composition) | 20% of Cetiol UT 0.5% of the essential oil mixture shown above — 4% of decyl glucoside | | 20% of Cetiol UT 0.5% of the premixed essential oil mixture shown above 4.5% of cyclodextrin 4% of decyl glucoside | |
| Results at 8 h - Intensity | +1% | NS | −11% | S |
| Results at 8 h - Hedonic value | 0% | NS | +10% | S |
| Results at 24 h - Intensity | +4% | NS | −8% | S |
| Results at 24 h - Hedonic value | −3% | NS | +6% | S |
| Results at 48 h - Intensity | +3% | NS | −7% | S |
| Results at 48 h - Hedonic value | −2% | NS | +8% | S |

NS = not significant
S = significant

It is clearly apparent, on reading the above data, that a composition according to the invention advantageously makes it possible to reduce the intensity of the axillary odour while rendering this odour more pleasant.

The invention claimed is:

1. Combination of active agents consisting of at least one essential oil, at least one cyclodextrin and at least one liquid fatty substance, wherein:
the cyclodextrin/essential oil weight ratio ranges from 5 to 12;
the cyclodextrin is present in said combination in a content ranging from 50% to 80% by weight, with respect to a total weight of the combination;
the liquid fatty substance is selected from the group consisting of liquid hydrocarbons, liquid fatty alcohols, liquid fatty esters, liquid fatty ethers, silicone oils, and mixtures thereof;
the liquid fatty substance is present in the combination in a content ranging from 15% to 40% by weight, with respect to the total weight of the combination; and
the essential oil is present in the combination in a content ranging from 0.00001% to 20% by weight, with respect to the total weight of the combination, and
wherein said combination is in a form of a paste.

2. Combination of active agents according to claim 1, wherein the essential oil is selected from the group consisting of geranium essential oil, citronella essential oil, cedar essential oil, sweet orange essential oil, Greek oregano essential oil, lemongrass essential oil, lemon catnip essential oil, rosemary essential oil, winter savory essential oil, thyme essential oil, lemon balm essential oil, lemon essential oil, eucalyptus essential oil, green or red mandarin essential oil, clove essential oil, cinnamon essential oil and their mixtures.

3. Combination of active agents according to claim 1 wherein the essential oil is selected from the group consisting of geranium essential oil, sweet orange essential oil and Greek oregano essential oil.

4. Combination according to claim 1, wherein the cyclodextrin is selected from the group consisting of α-cyclodextrin, β-cyclodextrin, and γ-cyclodextrin.

5. Combination according to claim 1, wherein the liquid fatty substance is selected from the group consisting of octyldodecanol, squalane, jojoba vegetable oil, caprylic/capric acid triglycerides, dicaprylyl ether, a mixture of n-undecane ($C_{11}$) and n-tridecane ($C_{13}$), and their mixtures.

6. Combination according to claim 1, wherein the cyclodextrin and the essential oil are in a cyclodextrin/essential oil weight ratio of between 8 and 12.

7. Combination according to claim 1, wherein the cyclodextrin is present in said combination in a content ranging from 50% to 70% by weight, with respect to the total weight of the combination.

8. Combination according to claim 1, wherein the liquid fatty substance is present in the combination in a content ranging from 20% to 30% by weight, with respect to the total weight of the combination.

9. Process for the preparation of a combination of active agents as defined in claim 1, comprising the stages of:
mixing the essential oil with the liquid fatty substance, and
adding the cyclodextrin,
then mixing.

10. Combination of active agents capable of being obtained according to a process consisting of the steps of:
mixing at least one essential oil with at least one liquid fatty substance, and
adding at least one cyclodextrin, wherein a cyclodextrin/essential oil weight ratio ranges from 5 to 12,
then mixing,
wherein:
the cyclodextrin is present in said combination in a content ranging from 50% to 80% by weight, with respect to a total weight of the combination;
the liquid fatty substance is selected from the group consisting of liquid hydrocarbons, liquid fatty alcohols, liquid fatty esters, liquid fatty ethers, silicone oils, and mixtures thereof;
the liquid fatty substance is present in the combination in a content ranging from 15% to 40% by weight, with respect to the total weight of the combination; and
the essential oil is present in the combination in a content ranging from 0.00001% to 20% by weight, with respect to the total weight of the combination, and
wherein said combination is in a form of a paste.

11. Cosmetic and/or dermatological composition comprising, in a physiologically acceptable medium, the combination as defined in claim 1.

12. Composition according to claim 11, wherein the essential oil is present in a content of between 0.00001% and 20% by weight, with respect to the total weight of the composition.

13. Composition according to claim 11, wherein the essential oil is present in a content of between 0.1% and 5% by weight, with respect to the total weight of the composition.

14. Composition according to claim 11, wherein the cyclodextrin is present in a content of between 0.01% and 40% by weight, with respect to the total weight of the composition.

15. Composition according to claim 11, wherein the cyclodextrin is present in a content of between 0.5% and 10% by weight, with respect to the total weight of the composition.

16. Composition according to claim 11, wherein the liquid fatty substance is present in a content of between 0.01% and 40% by weight, with respect to the total weight of the composition.

17. Composition according to claim 11, wherein the liquid fatty substance is present in a content of between 0.5% and 15% by weight, with respect to the total weight of the composition.

18. Composition according to claim 11, wherein it is provided in the form of an aqueous or aqueous/alcoholic solution which is optionally gelled, of a lotion, which is optionally a two-phase lotion, of an oil-in-water or water-in-oil or multiple emulsion, of an aqueous gel, of a dispersion of oils in an aqueous phase using spherules, these spherules being polymer particles or ionic and/or non-ionic lipid vesicles, or alternatively in the form of a powder, of a serum, of an oil, of a paste or of a soft stick.

19. Composition according to claim 11, wherein it furthermore comprises at least one additional active agent selected from the group consisting of surfactants, moisturizing agents, anti-wrinkle or anti-ageing agents, UV screening agents, desquamating agents, antioxidants, agents which stimulate the synthesis of dermal and/or epidermal macromolecules, dermo-decontracting agents, depigmenting agents, deodorant agents, fragrances and their mixtures.

20. Process for the preparation of a composition as defined in claim 11, comprising the preparation of a combination of active agents according to the following stages:
mixing the essential oil with the liquid fatty substance,
adding the cyclodextrin,
then mixing, and introducing this combination of active agents into a cosmetic or dermatological composition comprising a physiologically acceptable medium.

21. Composition according to claim 10, wherein the essential oil is selected from the group consisting of geranium essential oil, citronella essential oil, cedar essential oil, sweet orange essential oil, Greek oregano essential oil, lemongrass essential oil, lemon catnip essential oil, rosemary essential oil, winter savory essential oil, thyme essential oil, lemon balm essential oil, lemon essential oil, eucalyptus essential oil, green or red mandarin essential oil, clove essential oil, cinnamon essential oil and their mixtures.

* * * * *